(12) United States Patent
Davies

(10) Patent No.: US 12,005,163 B2
(45) Date of Patent: Jun. 11, 2024

(54) PHASED ARRAY MICROWAVE SANITIZER FOR PATHOGENS

(71) Applicant: Rockwell Collins, Inc., Cedar Rapids, IA (US)

(72) Inventor: Orion Davies, Cedar Rapids, IA (US)

(73) Assignee: Rockwell Collins, Inc., Cedar Rapids, IA (US)

(*) Notice: Subject to any disclaimer, the term of this patent is extended or adjusted under 35 U.S.C. 154(b) by 361 days.

(21) Appl. No.: 17/335,629

(22) Filed: Jun. 1, 2021

(65) Prior Publication Data

US 2021/0386899 A1 Dec. 16, 2021

Related U.S. Application Data

(60) Provisional application No. 63/037,099, filed on Jun. 10, 2020.

(51) Int. Cl.
*A61L 2/12* (2006.01)
*A61L 9/18* (2006.01)
*H01Q 3/34* (2006.01)

(52) U.S. Cl.
CPC ........ *A61L 9/18* (2013.01); *A61L 2/12* (2013.01); *H01Q 3/34* (2013.01); *A61L 2209/11* (2013.01)

(58) Field of Classification Search
CPC ..... A61L 2/08; A61L 2/12; A61L 2/24; A61L 9/18
See application file for complete search history.

(56) References Cited

U.S. PATENT DOCUMENTS

| | | | |
|---|---|---|---|
| 5,098,665 A | 3/1992 | Katschnig et al. | |
| 7,658,891 B1* | 2/2010 | Barnes | C01B 13/11 128/205.28 |
| 8,524,445 B2* | 9/2013 | Sun | G01N 22/00 435/5 |

FOREIGN PATENT DOCUMENTS

| | | |
|---|---|---|
| EP | 3331323 A4 | 7/2018 |
| WO | 2004105808 A3 | 7/2005 |
| WO | 2019224392 A1 | 11/2019 |

OTHER PUBLICATIONS

Extended Search Report for European Application No. 21178634.8 dated Oct. 22, 2021, 8 pages.
Guo, Zhen-Dong et al., Centers for Disease Control and Prevention, ISSN: 1080-6059, vol. 26, No. 7, Jul. 2020, 5 pages.
Hung, Wan-Ting et al., "A focusing reflectarray and its application in microwave virus sanitizer", Radio Science, vol. 49, Issue 10, 15 pages.
Morawska, Lidia et al., "Airborne transmission of SARS-COV-2: The world should face the reality", Environ Int., Jun. 2020, 139, 105730, PMCID: PMC7151430, PMID: 32294574, Elsevier Public Health Emergency Collection, 6 pages.

(Continued)

*Primary Examiner* — Timothy C Cleveland
(74) *Attorney, Agent, or Firm* — Suiter Swantz IP

(57) ABSTRACT

A system and method for sterilizing recirculated airflow in closed environments, as well as certain types of material equipment includes electronically steered antenna (ESA) elements. The ESA elements operate in radio frequencies (RF). The ESA elements produce directed beams of microwave radiation to sterilize surfaces or volumes of air. The directivity gain associated with the beam forming increases RF energy density in the area where the beam is steered.

5 Claims, 10 Drawing Sheets

Doors close to form parabolic reflector end caps containing radiated energy within the irradiated volume

(56) References Cited

OTHER PUBLICATIONS

Sun, Chi-Kuang et al., "Resonant Dipolar Coupling of Microwaves with Confined Acoustic Vibrations in a Rod-shaped Virus", Scientific Reports, 7:4611, DOI: 10. 1038/s41598-017-04089-7, Published Online Jul. 4, 2017, 9 pages.

Van Doremalen, Neeltje et al., "Aerosol and Surface Stability of SARS-COV-2 as Compared with SARS-COV-1", N. Engl. J. Med, Mar. 17, 2020, NEJMc2004973, doi: 10.1056/NEJMc2004973, PMCID: PMC7121658, PMID: 32182409, NEJM Group Public Health Emergency Collection, 5 pages.

\* cited by examiner

FIG.1

Example of eight steering profile variants

| Antenna in Use | Spacing Between Antenna and Virus Sample | Simulated Peak Power Density (Input Power = 1W) | Death Rate |
|---|---|---|---|
| Slot array antenna | 80 mm | 7.5 $mW/cm^2$ | 7% |
| | 30 mm | 8.9 $mW/cm^2$ | 53% |
| Focusing reflectarray | 178 mm | 27.0 $mW/cm^2$ | 93% |

FIG.10

PHASED ARRAY MICROWAVE SANITIZER FOR PATHOGENS

PRIORITY

The present application claims the benefit under 35 U.S.C. § 119(e) of U.S. Provisional App. No. 63/037,099 (filed Jun. 10, 2020), which is incorporated herein by reference.

BACKGROUND

Incidence of widespread, novel pathogens and resulting pandemics are increasing. Pandemic responses often necessitate quarantine operations with a potential to severely impact global industries and economies of entire nations.

Air handling systems for closed environments (e.g., hospital wards, airplane cabins, airport terminals, commuter rail cars, university buildings, cubicle office spaces, indoor auditoriums, etc.) are a significant vector for transmission of airborne respiratory pathogens. Medical facilities have a continual need to sanitize their equipment that requires copious amounts of chemical cleaning agents.

Recent studies published by the National Center for Biotechnology Information have shown that pathogens do not spread only by respiratory droplets that settle onto surfaces within a relatively short distance of approximately two meters (six feet), but also as microscopic airborne particles, or aerosols that are small enough to be transported by air current. Such small droplets are free to travel in the air and carry their viral content meters and tens of meters from their origin. Those droplets remain viable and infectious in aerosols for hours and on surfaces up to days. The viability of these pathogens to infect human beings does not decrease as readily when in aerosol form as it does in droplet form on surfaces.

Air handling systems in enclosed environments (hospital rooms, airplane cabins, office environments, etc.) are a significant vector for the spread of these pathogens in aerosol form.

SUMMARY

In one aspect, embodiments of the inventive concepts disclosed herein are directed to a system and method for sterilizing recirculated airflow in closed environments, as well as certain types of material equipment. The system includes electronically steered antenna (ESA) elements. The ESA elements operate in radio frequencies (RF). The ESA elements produce directed beams of microwave radiation to sterilize surfaces or volumes of air. The directivity gain associated with the beam forming increases RF energy density in the area where the beam is steered.

It is to be understood that both the foregoing general description and the following detailed description are exemplary and explanatory only and should not restrict the scope of the claims. The accompanying drawings, which are incorporated in and constitute a part of the specification, illustrate exemplary embodiments of the inventive concepts disclosed herein and together with the general description, serve to explain the principles.

BRIEF DESCRIPTION OF THE DRAWINGS

The numerous advantages of the embodiments of the inventive concepts disclosed herein may be better understood by those skilled in the art by reference to the accompanying figures in which:

FIG. 1 shows graphs of pathogen viability under various conditions and on various surfaces;

FIG. 10 shows a table of antenna peak power, distance, and pathogen death rates;

DETAILED DESCRIPTION

Figure 2:
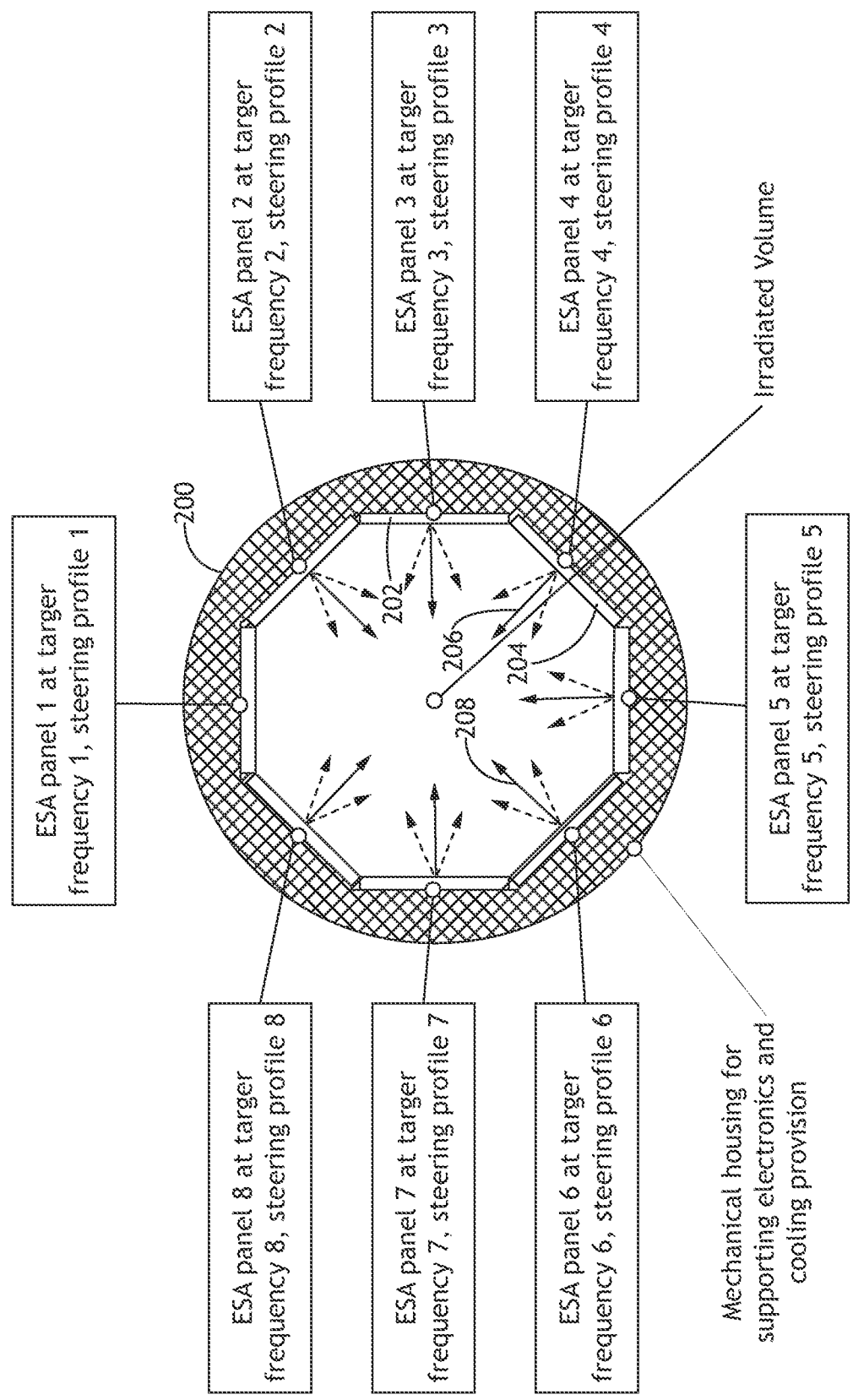
FIG. 2 shows a cross-sectional view of a sterilizing chamber according to an exemplary embodiment.

Before explaining at least one embodiment of the inventive concepts disclosed herein in detail, it is to be understood that the inventive concepts are not limited in their application to the details of construction and the arrangement of the components or steps or methodologies set forth in the following description or illustrated in the drawings. In the following detailed description of embodiments of the instant inventive concepts, numerous specific details are set forth in order to provide a more thorough understanding of the inventive concepts. However, it will be apparent to one of ordinary skill in the art having the benefit of the instant disclosure that the inventive concepts disclosed herein may be practiced without these specific details. In other instances, well-known features may not be described in detail to avoid unnecessarily complicating the instant disclosure. The inventive concepts disclosed herein are capable of other embodiments or of being practiced or carried out in various ways. Also, it is to be understood that the phraseology and terminology employed herein is for the purpose of description and should not be regarded as limiting.

As used herein a letter following a reference numeral is intended to reference an embodiment of the feature or element that may be similar, but not necessarily identical, to a previously described element or feature bearing the same reference numeral (e.g., 1, 1a, 1b). Such shorthand notations are used for purposes of convenience only, and should not be construed to limit the inventive concepts disclosed herein in any way unless expressly stated to the contrary.

Further, unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of embodiments of the instant inventive concepts. This is done merely for convenience and to give a general sense of the inventive concepts, and "a" and "an" are intended to include one or at least one and the singular also includes the plural unless it is obvious that it is meant otherwise.

Finally, as used herein any reference to "one embodiment," or "some embodiments" means that a particular element, feature, structure, or characteristic described in connection with the embodiment is included in at least one embodiment of the inventive concepts disclosed herein. The appearances of the phrase "in some embodiments" in various places in the specification are not necessarily all referring to the same embodiment, and embodiments of the inventive concepts disclosed may include one or more of the features expressly described or inherently present herein, or any combination of sub-combination of two or more such features, along with any other features which may not necessarily be expressly described or inherently present in the instant disclosure.

Broadly, embodiments of the inventive concepts disclosed herein are directed to a system and method for sterilizing recirculated airflow in closed environments, as well as certain types of material equipment. The system includes electronically steered antenna (ESA) elements. The ESA elements operate in radio frequencies (RF).

The ESA elements produce directed beams of microwave radiation to sterilize surfaces or volumes of air. The directivity gain associated with the beam forming increases RF energy density in the area where the beam is steered.

Figure 1:
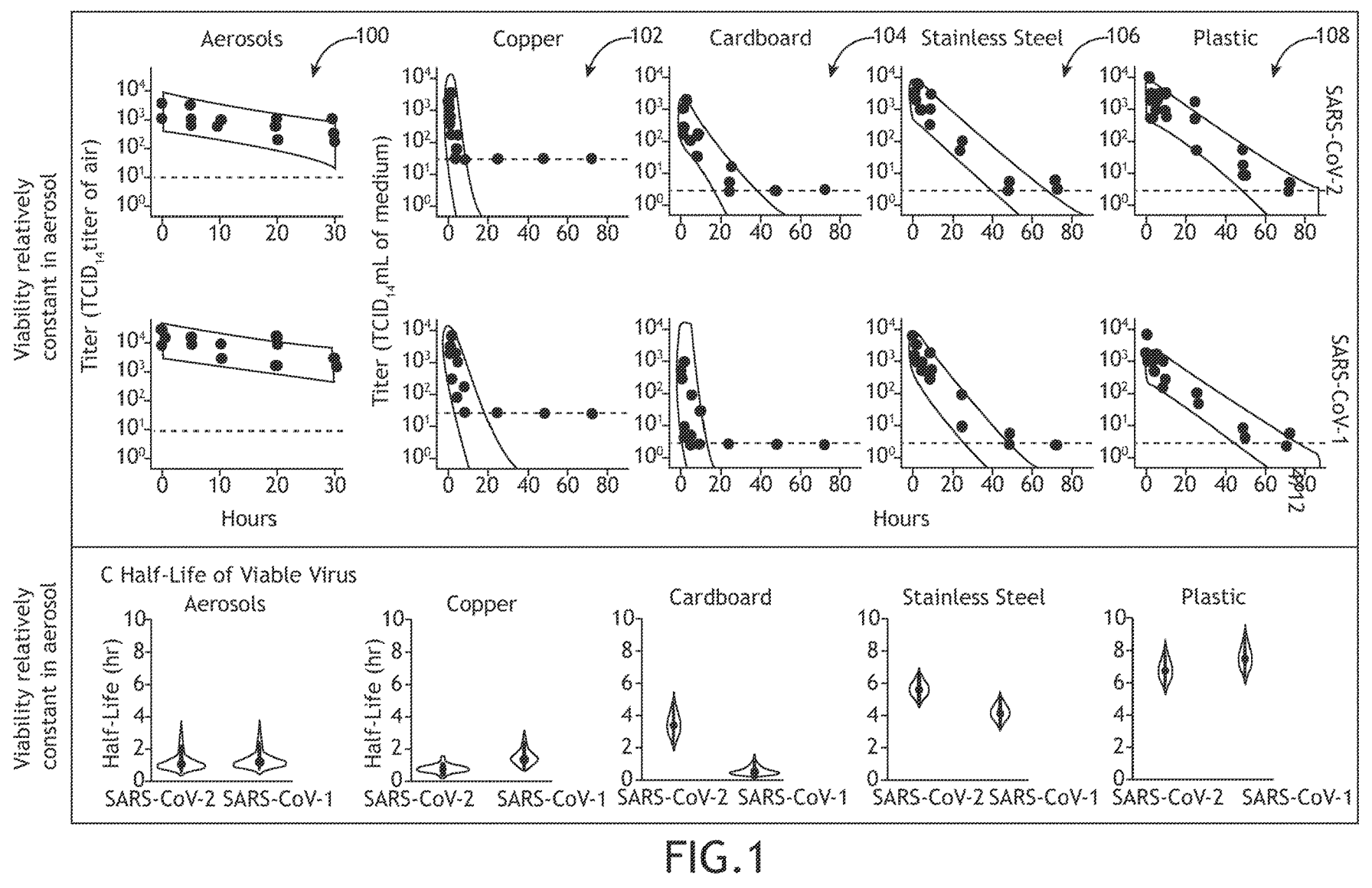

Referring to FIG. 1, graphs of pathogen viability under various conditions and on various surfaces is shown. The quantity of viable virus (titers) remains relatively constant in an aerosol 100 compared to how fast they decay on copper 102, cardboard 104, stainless steel 106, or plastic 108 surfaces. Likewise, the half-life some viruses (for example, SARS-Covid 1 and SARS-Covid 2) exceeds three hours in aerosol form. Those types of pathogens may remain in the air as viable disease vectors for hours. They may be picked up by air circulation systems while still infectious.

Referring to FIG. 2, a cross-sectional view of a sterilizing chamber 200 according to an exemplary embodiment is shown. The sterilizing chamber 200 is defined by a plurality of ESA panels 202, 204. The plurality of ESA panels 202, 204 are disposed to irradiate the volume enclosed by the chamber 200. In one exemplary embodiment, the ESA panels 202, 204 comprise eight ESA panels 202, 204 in an octagonal arrangement forming the interior walls of the chamber 200.

Each ESA panels 202, 204 produces a steerable beam 206, 208 that scans the interior volume. Pathogens in the interior volume may be neutralized via exposure to radiation from the ESA panels 202, 204.

Each ESA panel 202, 204 may be steered independently to follow a different steering profile to irradiate any particles within the volume multiple times from multiple angles of incidence as they travel through the chamber 200. Each ESA panel 202, 204 may transmit RF energy at a different frequency from the others, with enough separation in the frequency domain to avoid formation of null zones (regions within the volume where the net energy is close to zero) due to deconstructive interference. The ESA panels 202, 204 in this exemplary embodiment can be designed to radiate at specific target frequencies determined by the RF absorption spectra of certain pathogens such as rod-shaped influenza particles and spherical-shaped coronavirus particles.

Figure 3:
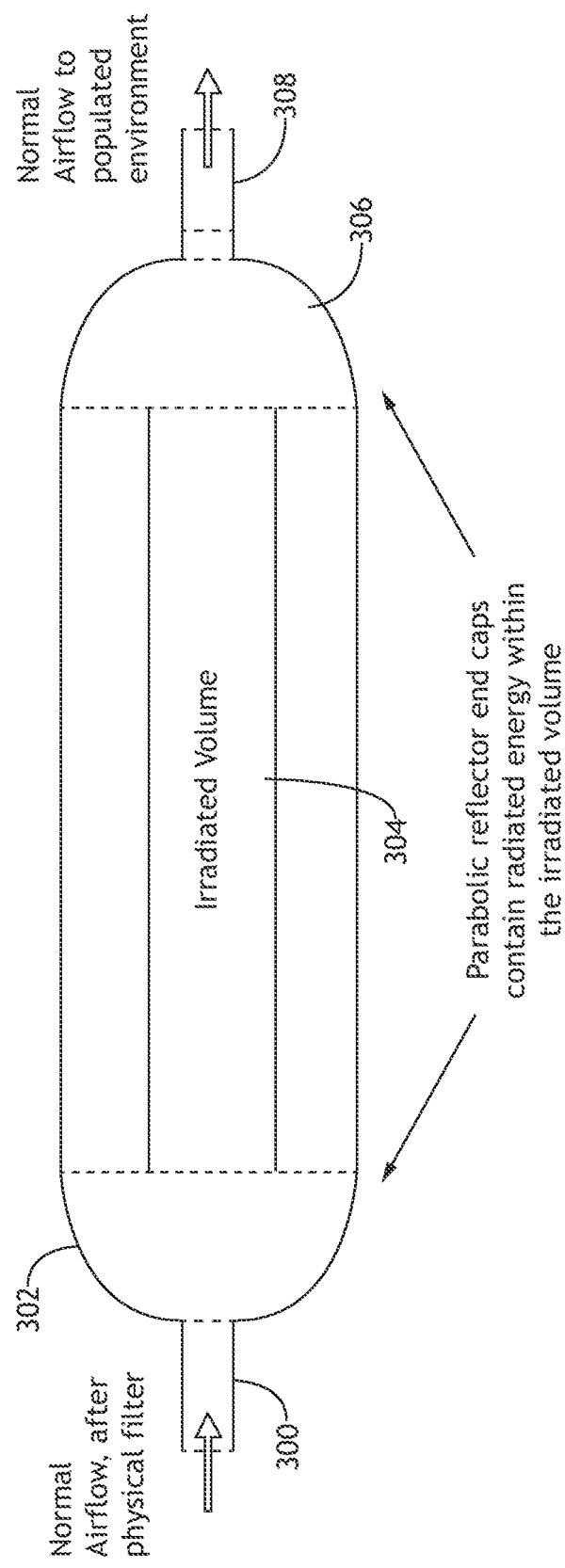
FIG. 3 shows a side view of a sterilizing chamber according to an exemplary embodiment.

Referring to FIG. 3, a side view of a sterilizing chamber 304 according to an exemplary embodiment is shown. The sterilizing chamber 304, defined by a plurality of ESA panels, is further defined by parabolic reflectors 302, 306 configured to retain reflected radiation and sidelobe radiation from the ESA panels within the chamber 304.

In at least one embodiment, where the chamber 304 is configured to sterilize air volumes, the parabolic reflectors 302, 306 may define an input 300 and an output 308 respectively. An airflow system may control the speed of airflow within the chamber 304 to optimize dwell time; alternatively, or in addition, the chamber 304 may include a manifold system to extend the functional airflow path within the chamber 304. Alternatively, or in addition, other mechanisms to extend dwell time within the enclosed volume may include a dielectric material that causes turbulence or a pump to increase internal pressure while limiting output via a regulator may increase dwell time.

Figure 4:
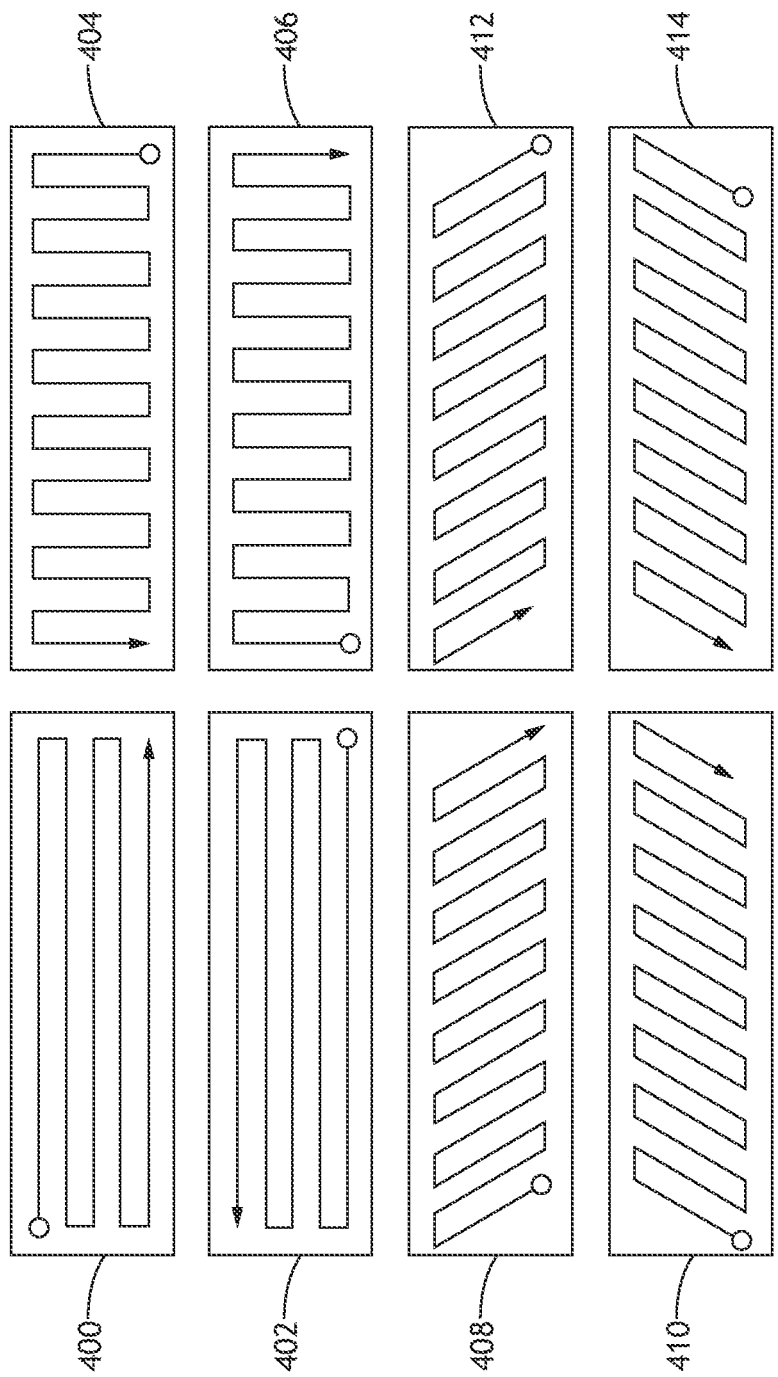
FIG. 4 shows scanning patterns according to exemplary embodiments.

Referring to FIG. 4, scanning patterns 400, 402, 404, 406, 408, 410, 412, 414 according to exemplary embodiments are shown. Each ESA panel defining a sterilizing chamber may be configured to produce a beam that scans a regular pattern 400, 402, 404, 406, 408, 410, 412, 414 of the contained volume to ensure the entire volume is sufficiently irradiated for a sufficient duration to destroy pathogens generally or specific pathogens. It may be appreciated that radiation frequencies may be specific to certain pathogens; that is to say certain pathogens are more vulnerable to (more absorbent of) certain radiation frequencies. Where specific pathogens are a concern, the ESA panels may be configured to the most effective radiation frequencies. Furthermore, it may be appreciated that the duration of irradiation may be defined by a desired threshold of pathogen destruction; for example, an exposure time of 15 minutes may produce approximately 93% pathogen destruction.

In at least one embodiment, ESA panels may be configured for different scanning patterns 400, 402, 404, 406, 408, 410, 412, 414. For example, a first set of ESA panels may employ a lateral scanning pattern 400 while a second set of ESA panels simultaneously employ a vertical scanning pattern 404. In at least one embodiment, different scanning patterns 400, 402, 404, 406, 408, 410, 412, 414 may prevent incidental interference that reduces dwell time at the desired frequency. Conversely, different scanning patterns 400, 402, 404, 406, 408, 410, 412, 414 may ensure that the ESA panels are always maintaining a threshold level of irradiation in every unit volume of the chamber.

Figure 5:
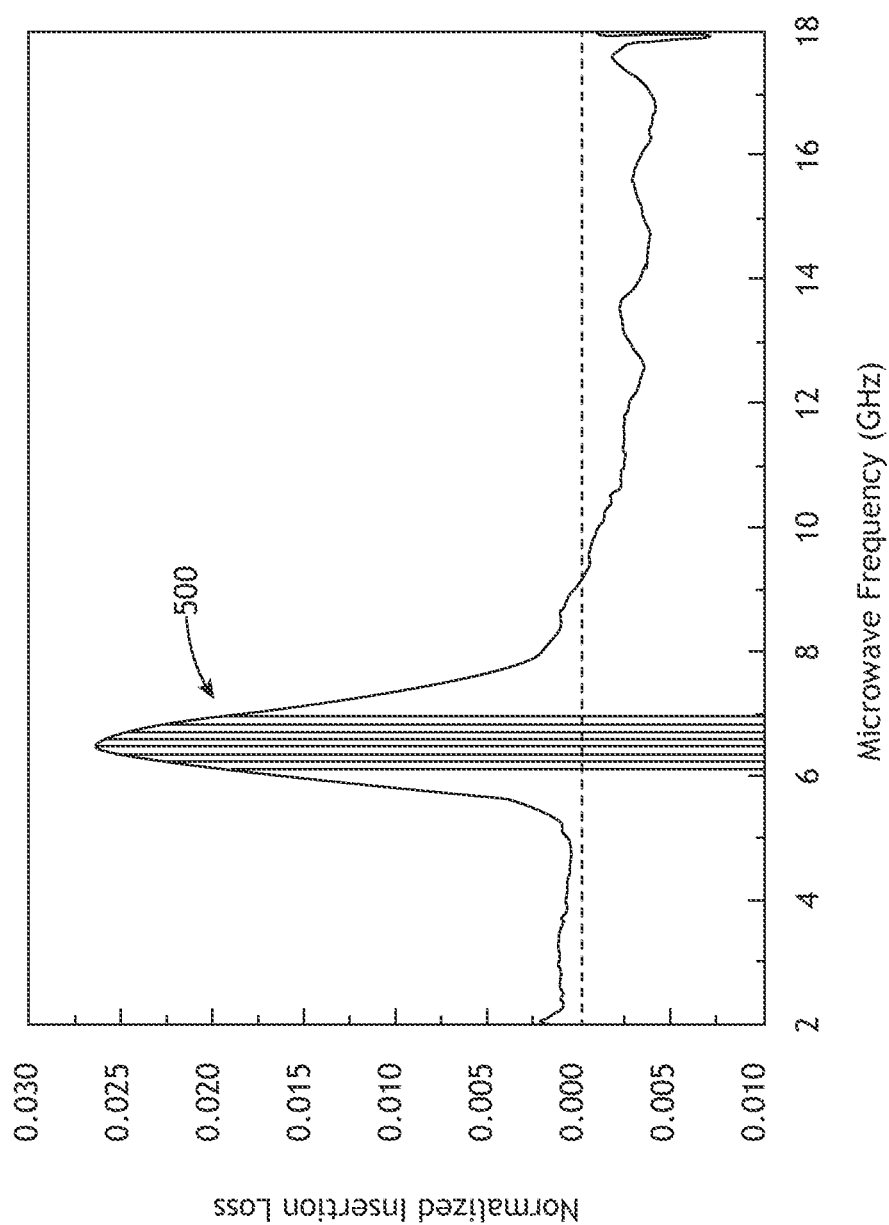
FIG. 5 shows a graph of absorption bands for an exemplary pathogen.

Referring to FIG. 5, a graph of absorption bands for an exemplary pathogen is shown. The absorption band 500 for a rod-shaped virus falls between 6 and 7 GHz. In at least one embodiment, a sterilization chamber defined by ESA panels configured for beam forming in 8 separate frequencies within that range sterilizes the internal volume to an arbitrary threshold based on total duration of exposure.

Figure 6:
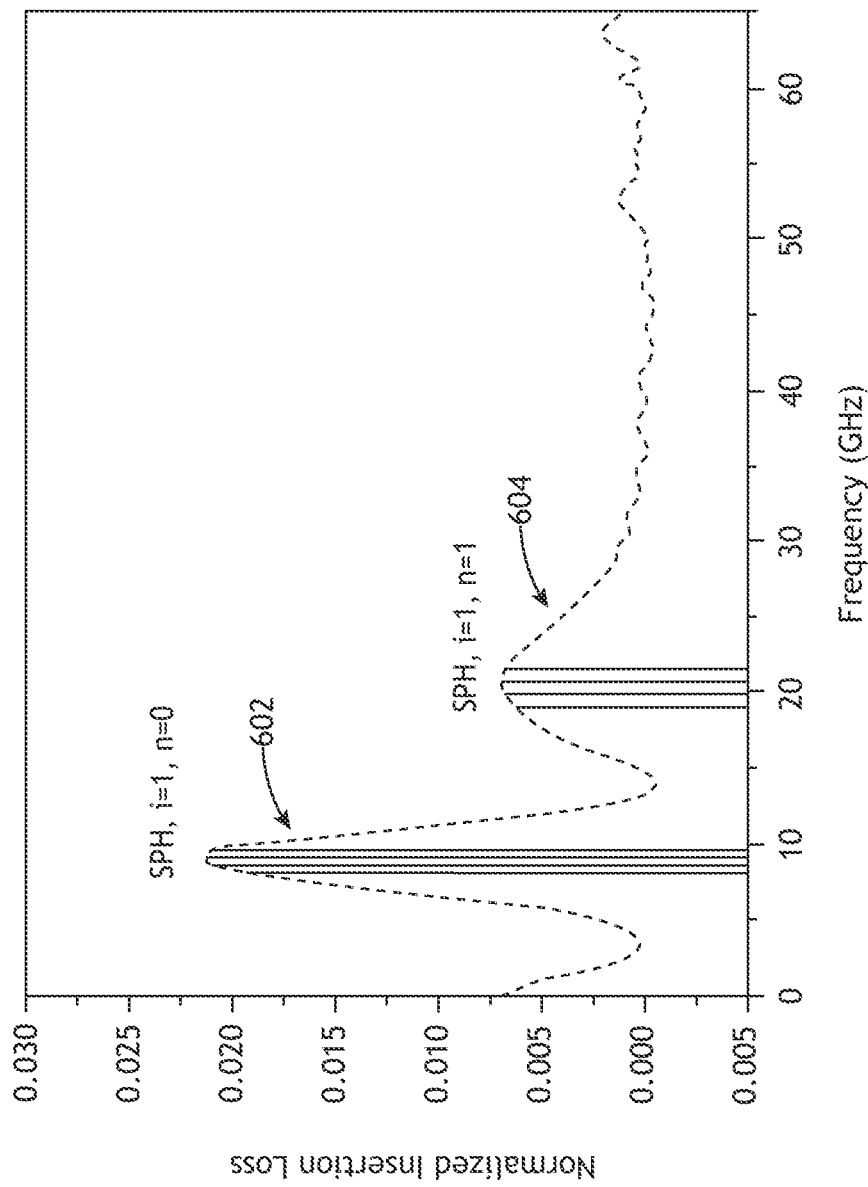
FIG. 6 shows a graph of absorption bands for an exemplary pathogen.

Referring to FIG. 6, a graph of absorption bands for an exemplary pathogen is shown. Absorption bands 600, 602 for a spherical-shaped virus fall between 8 and 10 GHz and 19 and 21 GHz respectively. In at least one embodiment, a sterilization chamber defined by ESA panels configured for beam forming in 8 separate frequencies within those ranges sterilizes the internal volume to an arbitrary threshold based on total duration of exposure. It may be appreciated that ESA panels may be configured to separately for maximum effectiveness against specific pathogens. Alternatively, or in addition, the sterilization chamber may be configured with different sets of ESA panels configured for different frequency ranges. In at least one embodiment, the ESA panels may be configured for maximum effectiveness against specific pathogens at different times; for example, the ESA panels may be configured for 6 to 7 GHz for a first dwell time and 8 to 10 GHz and 19 to 21 GHz for a second dwell time.

Figure 7:
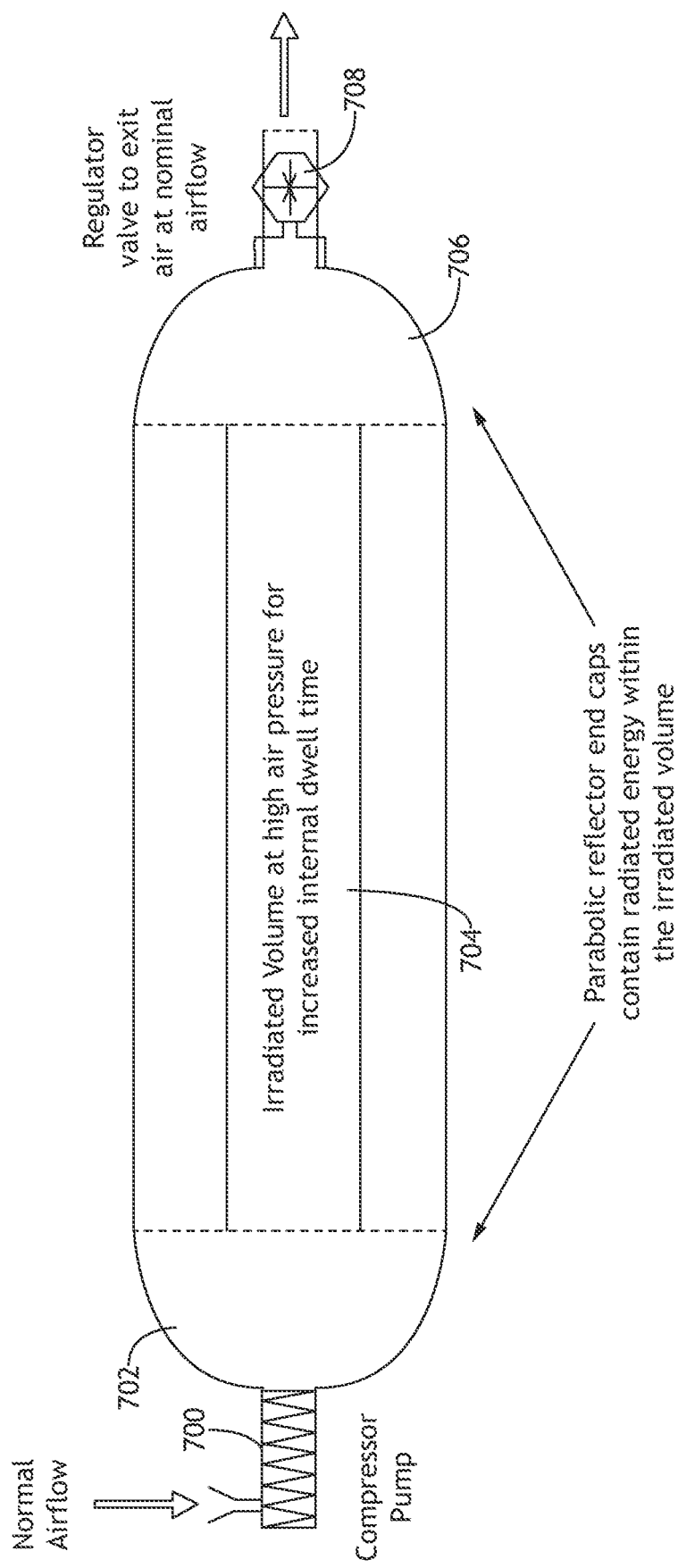
FIG. 7 shows a side view of a sterilizing chamber according to an exemplary embodiment.

Referring to FIG. 7, a side view of a sterilizing chamber 704 according to an exemplary embodiment is shown. The sterilizing chamber 704, defined by a plurality of ESA panels, is further defined by parabolic reflectors 702, 706 configured to retain reflected radiation and sidelobe radiation from the ESA panels within the chamber 704.

In at least one embodiment, where the chamber 704 is configured to sterilize air volumes, the parabolic reflectors 702, 706 may define an input compressor 700 and an output regulator 708 respectively. The compressor 700 receives an airflow at a first, normal rate, and compresses the air to a higher pressure inside the sterilizing chamber 704. The regulator 708 slowly releases the higher-pressure air from inside the chamber 708. Increased pressure allows for increased dwell time, a smaller chamber volume per flow-rate of air, or both.

Figure 8:
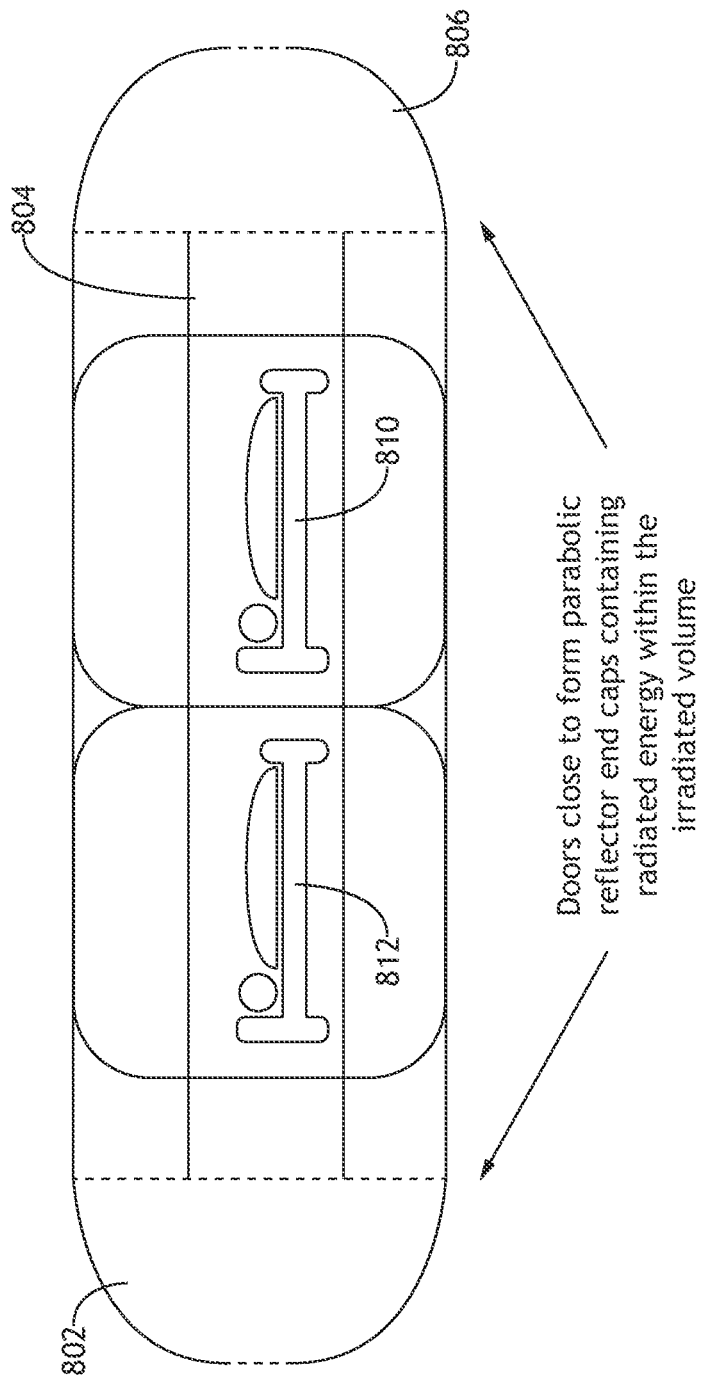
FIG. 8 shows a side view of a sterilizing chamber according to an exemplary embodiment.

Referring to FIG. 8, a side view of a sterilizing chamber 804 according to an exemplary embodiment is shown. The sterilizing chamber 804, defined by a plurality of ESA panels, is further defined by parabolic reflectors 802, 806 configured to retain reflected radiation and sidelobe radiation from the ESA panels within the chamber 804.

In at least one embodiment, where the chamber 804 is configured to sterilize equipment 810, 812, the parabolic reflectors 802, 806 define doors into the sterilizing chamber 804. Equipment 810, 812, such as hospital beds or other hospital equipment that is large and difficult to reliably sterilize, is loaded into the chamber 804 and the parabolic reflectors 802, 806 are closed. The equipment 810, 812 is then irradiated by ESA panels that define the chamber 804 for a dwell time and at all angles, sufficient to destroy pathogens of interest to within an arbitrary threshold.

Figure 9:
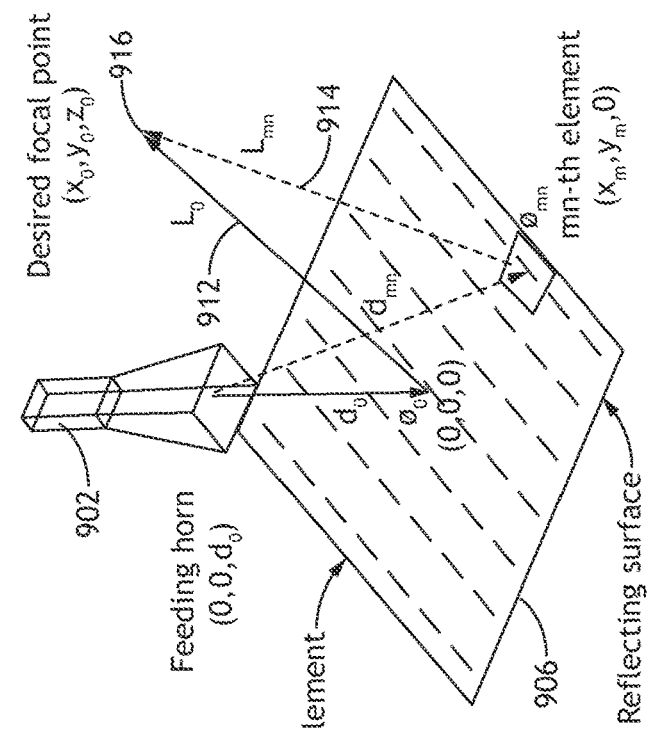
FIG. 9 shows a far-field array useful in exemplary embodiments.
Figure 9:
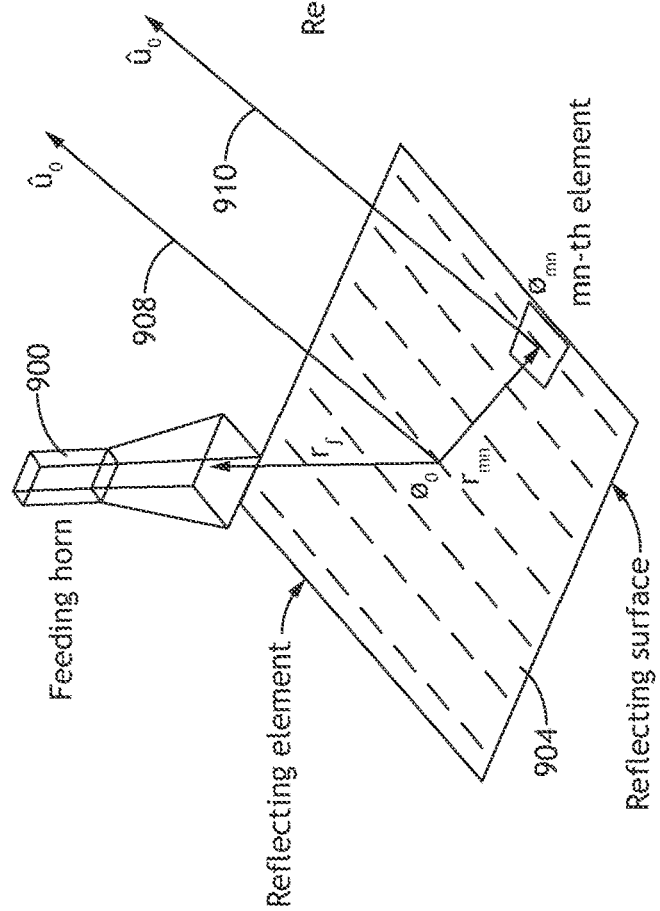

Referring to FIG. 9, a far-field array useful in exemplary embodiments is shown. Radiation from a feeding antenna 900 is directed to a reflecting surface 904 and then reradiated by phase-arranged reflecting elements of the reflecting surface 904. The reradiated waves 908, 910 form a planar phase front to some desired far-field direction. The wavefront of the reradiated waves 908, 910 remain co-phasal in the desired far-field direction. The phase of the wavefront associated with a given reflecting element is the summation of the propagation phase delay from the feeding antenna 900 to the reflecting element, the reflection phase of that reflecting element, and the propagation phase delay from that reflecting element to the desired main beam direction.

Alternatively, radiation from a feeding antenna 902 is directed to a reflecting surface 906 and the reradiated waves 912, 914 are focused onto a desired focal point 916 which may be mostly in the radiating near-field region of the reflecting surface 906. The focusing reflecting surface 906 concentrates microwave (or other radiation) power onto the focal point 916. Focusing power at a focal point means that the waves reradiated from the reflecting elements should be co-phasal or in phase at the desired focal point 916.

Referring to FIG. 10, a table of antenna peak power, distance, and pathogen death rates is shown. Time-averaged power densities of three different radiation array configurations with slot array at 80 mm, slot array at 30 mm, and focusing reflecting surface at 178 mm were previously tested. For all three cases, the input power levels are fixed at 1 W. In these three tested configurations, virus samples were illuminated for 15 minutes and the death rate of the virus of each sample was recorded. The death rates of the virus samples were 7%, 53%, and 93%, respectively. The results show that focusing outperforms far-field high-gain slot array antennas in virus sanitization.

Embodiments of the present disclosure are directed to a cavity that encloses a treatment volume; the walls of the cavity are formed by ESA panels. In at least one embodiment, ESA panels are mounted on the walls of the cavity or the entire surface area of the wall of the cavity is the radiator of the ESA itself. Parabolic reflector end caps keep any stray energy from side lobes or reflections from escaping the volume. The parabolic reflector with a feed port in the center appears as a black body to any radiation that hits it. Radiation is be reflected back inside of the chamber.

Radiation from the ESAs excites acoustic resonant modes in the pathogen particles and cause them to vibrate enough that their geometry changes on the outer surface. Multiple different frequency ranges target multiple pathogens instead of just one. Different pathogens are affected by different frequencies, so one set of ESA panels may be configured to target pathogens like coronavirus while others target pathogens like flu virus.

In at least one embodiment, each panel is steered around separately and particles traveling through the treatment volume can be irradiated from multiple angles of incidents many times to eliminate effects of shading. Such embodiments may be particularly advantageous when scaled up to sanitize things such as hospital beds where it may be difficult to illuminate all surfaces with existing UV point sources.

Embodiments of the present disclosure may be suitable for inclusion in the air filtration system of mobile platforms such as aircraft.

It is believed that the inventive concepts disclosed herein and many of their attendant advantages will be understood by the foregoing description of embodiments of the inventive concepts disclosed, and it will be apparent that various changes may be made in the form, construction, and arrangement of the components thereof without departing from the broad scope of the inventive concepts disclosed herein or without sacrificing all of their material advantages; and individual features from various embodiments may be combined to arrive at other embodiments. The form herein before described being merely an explanatory embodiment thereof, it is the intention of the following claims to encompass and include such changes. Furthermore, any of the features disclosed in relation to any of the individual embodiments may be incorporated into any other embodiment.

What is claimed is:

1. A method for sterilizing an enclosed volume comprising:
    defining the enclosed volume with a plurality of electronically steered array antenna panels and radio opaque parabolic reflector endcaps;
    determining one or more frequency ranges for the plurality of electronically steered array antenna panels based on characteristics of a target pathogen;
    applying signals to each of the plurality of electronically steered array antenna panels to produce steerable beams in the one or more frequency ranges; and
    reflecting sidelobes produced by the plurality of electronically steered array antenna panels within the enclosed volume,
    wherein the radio opaque parabolic reflector endcaps define doors into the enclosed volume.

2. The method of claim 1, wherein the one or more frequency ranges includes a range of 6 GHz to 7 GHz.

3. The method of claim 2, wherein the one or more frequency ranges includes a range between 8 GHz and 10 GHz, and a range between 19 GHz and 21 GHz.

4. The method of claim 1, further comprising:
    steering a beam along a first scanning pattern via a first set of electronically steerable array antenna panels in the plurality of electronically steered array antenna panels; and steering a beam along a second scanning pattern via a second set of electronically steerable array antenna panels in the plurality of electronically steered array antenna panels.

5. The method of claim 1, further comprising:

increasing air pressure within the enclosed volume via a compressor; and releasing air from within the enclosed volume via a regulator, wherein the compressor and regulator are configured to increase dwell time of irradiation within the enclosed volume.

\* \* \* \* \*